(12) United States Patent
Fischer et al.

(10) Patent No.: US 7,729,470 B2
(45) Date of Patent: *Jun. 1, 2010

(54) MEDICAL DEVICE WITH RADIATION-HEATED SUBJECT-CONTACTING COMPONENT

(75) Inventors: Daniel Fischer, Erlangen (DE); Jasmina Orman, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 106 days.

This patent is subject to a terminal disclaimer.

(21) Appl. No.: 11/837,664

(22) Filed: Aug. 13, 2007

(65) Prior Publication Data

US 2008/0253512 A1    Oct. 16, 2008

(30) Foreign Application Priority Data

Aug. 16, 2006    (DE)    ........................ 10 2006 038 067

(51) Int. Cl.
*A61B 6/04* (2006.01)

(52) U.S. Cl. ........................................ 378/37; 378/208
(58) Field of Classification Search ................ 378/208, 378/209, 37
See application file for complete search history.

(56) References Cited

U.S. PATENT DOCUMENTS

| | | | |
|---|---|---|---|
| 2005/0265518 A1* | 12/2005 | Aubel | 378/37 |
| 2007/0139799 A1* | 6/2007 | Ramsauer | 359/837 |
| 2008/0107232 A1* | 5/2008 | Bohrisch et al. | 378/37 |
| 2008/0247508 A1* | 10/2008 | Harrington et al. | 378/37 |

FOREIGN PATENT DOCUMENTS

DE    10 2004 043 532 A1    3/2006

* cited by examiner

*Primary Examiner*—Hoon Song
(74) *Attorney, Agent, or Firm*—Schiff Hardin LLP

(57) ABSTRACT

A medical device has a compression plate for compression of a subject and/or a subject table for placement of a subject, and at least one radiation source that emits electromagnetic radiation. The compression plate and/or the subject table can be heated by the electromagnetic radiation radiated by the at least one radiation source.

18 Claims, 2 Drawing Sheets

MEDICAL DEVICE WITH RADIATION-HEATED SUBJECT-CONTACTING COMPONENT

BACKGROUND OF THE INVENTION

1. Field of the Invention

The invention concerns a medical device with a compression plate for compression of a subject and/or a subject table for placement of a subject for a medical examination.

2. Description of the Prior Art

In the medical field a number of the widely-varied devices exist that exhibit a compression plate and/or a subject table. In nearly every medical examination a subject to be examined is placed on a subject table in order to implement the examination. The subject tables used for this can be of different design; for example, they can serve for placement of an entire patient (as are used, for instance, in magnetic resonance tomography and computed tomography) or can also serve only for placement of a specific body part of the patient (for instance in orthopedic x-ray examinations or in mammography examinations).

Among other things, medical devices with compression plates are used for mammography or for implementation of a biopsy. In particular, the course of a biopsy can be monitored by many different analytical methods.

The compression of a (normally female) breast that is required for a mammogram today is frequently implemented with rigid, inflexible compression plates. For example, the compression plates used for this typically are formed of polymethylmethacrylate (PMMA).

In mammography the compression of the breast serves on the one hand to reduce the thickness of the breast tissue to be x-rayed, so that scatter rays are reduced. Additionally, in the examination the breast is extended from the thorax of the patient by the compression of the breast, so a surface-proximal examination of the breast is enabled.

The compression of the breast is achieved by the compression device together with a rigid compression plate being displaced relative to a subject table on which the subject to be examined or to be compressed is supported. The compression of the breast or of the subject by means of a rigid compression plate (for example in a mammogram) normally does not allow a flexible consideration of an anatomy of the female breast varying from patient to patient. The compression of the breast with a rigid compression plate therefore normally leads to pain being experienced by the patient or damage to the subject to be compressed (in the event of non-living subjects).

In the field of mammography, a large number of differently-shaped rigid compression plates that are adapted to different sizes and shapes of female breasts are made available so as to allow the technician to select and provide a compression plate best adapted for a specific patient. The compression thus can proceed more comfortably for the patient.

To increase the utilization of the mammography device, however, frequently no changing of the compression plates ensues, in order to save time between mammography examinations and thereby increasing the patient throughput.

For examination of the breast of the patient by means of a mammography device, the breast is initially arranged on a subject table and is subsequently compressed by the compression plate.

Normally, both the compression plate and the subject table exhibit a surface temperature that coincides with the ambient temperature of the environment, normally room temperature of, for example, 20 degrees Celsius. Since the breast essentially exhibits the body temperature of the patient, i.e. approximately 37 degrees Celsius, the contact of the breast with the subject table as well as with the compression plate is perceived as uncomfortably cold by the patient.

The pain in the breast that is perceived by the patient during the compression as well as the feeling of cold occurring for the patient upon contact of the subject table or the compression plate with the breast leads to the patient having uncomfortable associations with having a mammogram.

SUMMARY OF THE INVENTION

An object of the present invention is to provide a medical device with which an examination and/or a treatment of a subject (in particular a patient) can be improved.

In a medical device of the aforementioned type, this object is achieved by the use of at least one radiation source radiating electromagnetic radiation, wherein the compression plate and/or the subject table is heated by the radiation radiated by the at least one radiation source. Heating of the compression plate and/or of the subject table can be achieved by the use of electromagnetic radiation, independent of the design and shape of the compression plate and/or the subject table since the feeding of the energy for heating of the compression plate and/or the subject table ensues without contact.

In principle an arbitrary wavelength spectrum of the electromagnetic radiation can be used to heat the compression plate and/or the subject table. In particular, x-rays can be used for heating of the compression plate and/or the subject table.

Furthermore, no installation effort at the compression plate and/or at the subject table is required in order to achieve a heating of the compression plate and/or of the subject table with the inventive medical device. For example, no heating plates must also be provided that may hinder examination of a subject to be examined by, for example, scattering magnetic fields or x-rays.

At least two radiation sources are advantageously provided in a medical device fashioned as a mammography device, with one radiation source irradiating the compression plate with electromagnetic radiation and the respective other radiation source irradiating the subject table with electromagnetic radiation, so that the irradiated surface of the compression plate and that of the subject table are both essentially heated by the electromagnetic radiation.

The temperature of the compression plate and/or of the subject table is adapted to the temperature of a subject to be examined or to a different, predeterminable temperature by the irradiation of the compression plate and/or of the subject table.

If the medical device has both a compression plate and a subject table, the at least one radiation source for heating the compression plate and the subject table is advantageously arranged essentially between the subject table and the compression plate. With such an arrangement, the top side of the subject table as well as the underside of the compression plate (thus those partial regions of the compression plate and the subject table that come into physical contact with the subject to be examined) are heated in a simple manner by the electromagnetic radiation emanating from the at least one radiation source.

The examination of a patient by means of the inventive medical device thus proceeds more comfortably and the examination or treatment of a patient is thereby improved.

In an embodiment of the invention the electromagnetic radiation exhibits a wavelength spectrum, with a first sub-range of the wavelength spectrum being in the infrared spectral range and a second part of the wavelength spectrum being in the spectral range visible to the human eye. By providing at least these two spectral ranges, an efficient heating of a surface region of the compression plate and/or a surface region of the subject table can ensue with the infrared spectral range of the electromagnetic radiation; and information visible to the patient or the physician can be shown in the same surface region by means of the visible spectral range In another embodiment of the invention, information can be projected onto the compression plate and/or the subject table by means of the visible spectral range of the electromagnetic radiation. For example, during the positioning of the subject to be examined on the subject table, the spatial dimensions of the detector surface exhibited by an x-ray detector (which is arranged below the subject table) can be projected onto the subject table.

It is likewise possible, for example, to project onto the subject table the size of a compression region of a compression plate that will compress the subject to be examined, in order to allow the breast to be positioned in a suitable manner. The compression region is the region of the compression plate coming into contact with the breast during the compression and provided for the contact with the breast.

By presentation of such information in the form of a projection on the compression plate and/or the subject table, the physician can adapt the position of the subject to be examined to the position of the x-ray detector, and possibly to the position of a compression plate, in a simple manner.

The projection can, for example, show examination parameters for the operation of the medical device or patient data that are projected onto the subject table and/or the compression plate. In principle, any optically-presentable information can be projected onto the subject table and/or the compression plate.

In a further embodiment of the invention, at least one sensor for detection of the temperature of the compression plate and/or at least one sensor for detection of the temperature of the subject table is/are provided. The heating or increase of the temperature of the compression plate and/or of the subject table can be tracked by means of the at least one sensor. If applicable, at least one further sensor for detection of intensity of the radiated electromagnetic radiation can be provided. The sensors for detection of the temperature can be, for example, infrared sensors. Pyroelectrics, thermo-elements, oscillating crystals, semiconductor temperature sensors and other temperature sensors for detection of the temperature of the compression plate and/or of the subject table can likewise be used. Normally such sensors for detection are used, which do not significantly interfere with the operation of the medical device and the examination of a subject to be examined.

In another embodiment variant of the invention, control and/or regulation of the temperature increase of the subject table and/or of a temperature increase of the compression plate is provided. Control of the temperature increase allows a predeterminable temperature (stored, for example, in a control device) of the compression plate and/or of the subject table to be set. For control of the temperature increase, the temperature of the compression plate and/or of the subject table that is detected by the at least one sensor serves as a reference for monitoring the temperature increase. If a regulator device is used, the temperature of the compression plate and/or of the subject table that is detected by the at least one sensor is supplied to the regulator device which thereupon regulates the power (emitted, for example, in the form of electromagnetic radiation) of the radiation source in order to reach or to maintain a predetermined temperature of the compression plate and/or of the subject table. The control and/or regulation of the temperature of the compression plate and/or of the subject table can ensue manually or automatically.

In a further embodiment of the invention, the compression plate and/or the subject table includes a device to slow decay of the temperature of the compression plate that occurs after the irradiation and/or decay of the temperature of the subject table that occurs after the irradiation. If the irradiation of the compression plate and/or of the subject table ends with the shut off of the electromagnetic radiation, cooling of the heated compression plate and/or of the heated subject table normally occurs.

It is frequently desired that the temperature of the compression plate and/or of the subject table that be increased relative to an environmental temperature and be retained over a longer time span so that, for example, reheating requires a smaller warming time of the compression plate and/or the subject table. For example, heat accumulators can be provided for this purpose. These can be realized both by heat-storing structures (for example honeycomb structures) or by the use of appropriate materials (normally materials with high heat capacity).

In a further embodiment of the invention, the radiation device from which electromagnetic radiation can be radiated onto the compression plate and/or the subject table is adjustable. A single radiation source for heating the compression plate and/or the subject table can be provided by changing the radiation direction of the electromagnetic radiation on the compression plate and/or the subject table. For example, the radiation source can be moved, controlled by means of a motor, such that the electromagnetic radiation alternatingly strikes the compression plate and the subject table. The warmable surface region of the compression plate and/or of the subject table can additionally be varied by changing the radiation direction.

In a preferred embodiment of the invention, the radiation direction of the electromagnetic radiation can be adjusted perpendicular to a surface normal of the subject table and/or perpendicular to a surface normal of the compression plate. This is advantageous, for example, when the subject table is fashioned as a cover of the x-ray detector. Heating of such a subject table over a longer time span would also lead to an unwanted increase of the temperature of the x-ray detector for which cooling is normally provided anyway.

In order to avoid a further heating of the subject table and thus of the x-ray detector, the direction of the electromagnetic radiation is adjusted such that the surface normal of the subject table is perpendicular to the radiation direction (propagation direction) of the electromagnetic radiation. The electromagnetic radiation then propagates parallel to the surface of the subject table, so essentially no further heat is produced by the electromagnetic radiation in the subject table.

In an embodiment of the invention, the compression plate and/or the subject table has in at least one sub-region, a coating that promotes conversion of the electromagnetic radiation striking the compression plate and/or the subject table into a temperature increase of the compression plate and/or of the subject table. The coating is selected such that electromagnetic radiation can be efficiently transduced into a temperature increase. In order to achieve an efficient transduction of electromagnetic energy into heat, the coating can be a layer system of various layers which exhibit different thermal and/or optical properties.

In order to be able to effect an efficient transduction of electromagnetic radiation into a temperature increase, a material is used that has a high absorption coefficient and a low specific heat capacity for the utilized wavelength spectral range of the electromagnetic radiation emanating from the radiation source; in the following this is called an absorption layer. A high absorption coefficient of the coating leads to an increased absorption of energy introduced by the electromagnetic radiation, and a low specific heat capacity leads to comparably little energy being required in order to achieve an increase of the temperature of this absorption layer.

In order to prevent a fast temporal decay of the temperature after the end of irradiation of the coating with electromagnetic radiation (which decay would be a direct consequence of the low specific heat capacity of the absorption layer), a second layer with a distinctly higher specific heat capacity can be provided directly below the absorption layer; the second layer is called a storage layer in the following.

A fast heating of the absorption layer occurs during the irradiation of the coating with electromagnetic radiation and an exchange of heat occurs by heat conduction between the absorption layer and the storage layer. Due to the higher specific heat capacity, the storage layer is heated significantly more slowly than the absorption layer. However, due to its significantly higher specific heat capacity, the heated storage layer can act as a heat accumulator. When the irradiation of the coating with electromagnetic radiation ends, the absorption layer cools much quicker than the storage layer due to the low specific heat capacity. The heat flow between absorption layer and the storage layer therefore reverses and the absorption layer is heated by the storage layer. Slowing of the decay of the temperature of the absorption layer is thus achieved.

The conversion of electromagnetic radiation into heat can ensue particularly efficiently when the optical properties of the coating of the compression plate and/or of the subject table and the wavelength spectrum of the electromagnetic radiation radiated by the at least one radiation source are adapted to one another. For this purpose, the coating can be adapted (as is known, for example, from the field of solar cells) in order to improve its efficiency—known as bandgap engineering. Alternatively, the electromagnetic radiation emanating from the radiation source can be tuned through its wavelength spectrum in order to be able to be utilized for various coatings with different optical properties.

The thickness of the layers of the coating—for instance absorption layer and storage layer—can be adapted to the expected average irradiation duration of the compression plate and/or the subject table with electromagnetic radiation and/or to the desired decay behavior of the temperature of the compression plate and/or of the subject table.

If the medical device is fashioned as an x-ray device, it is particularly advantageous that the coating on the compression plate and/or the subject table is essentially transparent for x-rays. The examination implemented with x-rays is thus at most negligibly influenced by the coating applied on the compression plate and/or the subject table, and the examination success is not endangered.

In the embodiment of the invention, the compression plate and/or the subject table is at least partially fashioned of a material in which the electromagnetic radiation striking the compression plate and/or the subject table is easily converted into a temperature increase of the compression plate and/or of the subject table. This represents an alternative possibility with regard to the use of the aforementioned coating of the compression plate and/or of the subject table.

Such materials forming the compression plate and/or the subject table can also be used in combination with the aforementioned coating. The explanations described above for the coating apply in an analogously to a material or multiple materials at least partially form the subject table, and by means of which the electromagnetic radiation striking the compression plate and/or the subject table can be efficiently converted into a temperature increase of the compression plate and/or of the subject table.

The material at least partially forming the compression plate and/or the subject table thereby advantageously has a defined surface region of the compression plate and/or of the subject table, so that the electromagnetic radiation radiated from the radiation source can be radiated onto the material in a geometrically simple manner.

The advantage of a material at least partially forming the compression plate and/or the subject table compared to the use of coating is that the material at least partially forming the compression plate and/or the subject table is normally less prone to wear than a coating of the compression plate and/or the subject table. The advantage of the use of a coating on the compression plate and/or the subject table is that this can be renewed relatively simply, as needed. Given the use of a material forming the compression plate and/or the subject table, the entire compression plate and/or the entire subject table normally has to be replaced upon damage or wear of the material.

The material at least partially forming the compression plate and/or the subject table is advantageously also substantially transparent for x-rays, so that it does not have a negative influence on the examination result of the subject to be examined in x-ray examinations.

In an advantageous embodiment of the invention, a radiation source emitting an electromagnetic radiation is provided, and a subject can be heated by means of the radiation radiating from the radiation source. In particular given a compression to be implemented for an examination with the medical device, a heating of the subject (for example a female breast) leads to a relaxation of the tissue. The breast tissue thus presents a lesser resistance to the compression plate and the subject table with the compression of the breast, and the examination is perceived as more comfortable. Moreover, a relaxed subject to be examined, for example relaxed breast tissue in the case of a mammogram, can be positioned more easily.

In a preferred embodiment of the invention, the electromagnetic radiation emanating from the radiation source to heat a subject exhibits an intensity and/or a wavelength spectrum that is adapted to the optical properties of the subject to be examined. The subject to be heated thus can be heated in a suitable manner. The intensity of the electromagnetic radiation striking the subject must not be selected so high as to lead to burning of the subject nor too low, so that no heating of the subject occurs.

An adaptation of the wavelength spectrum of the electromagnetic radiation to the subject to be heated is likewise normally required. For a human patient, a wavelength that is neither too short (for example in the ultraviolet spectral range or even in the x-ray spectral range) nor too long a wavelength (for example in the microwave range) must be selected.

For irradiation of the subject, the infrared spectral range of electromagnetic waves and an intensity that enables a gentle heating of the subject are advantageously used. For example, a conventional red light lamp can be used for this purpose.

DESCRIPTION OF THE PREFERRED EMBODIMENTS

Figure 1:
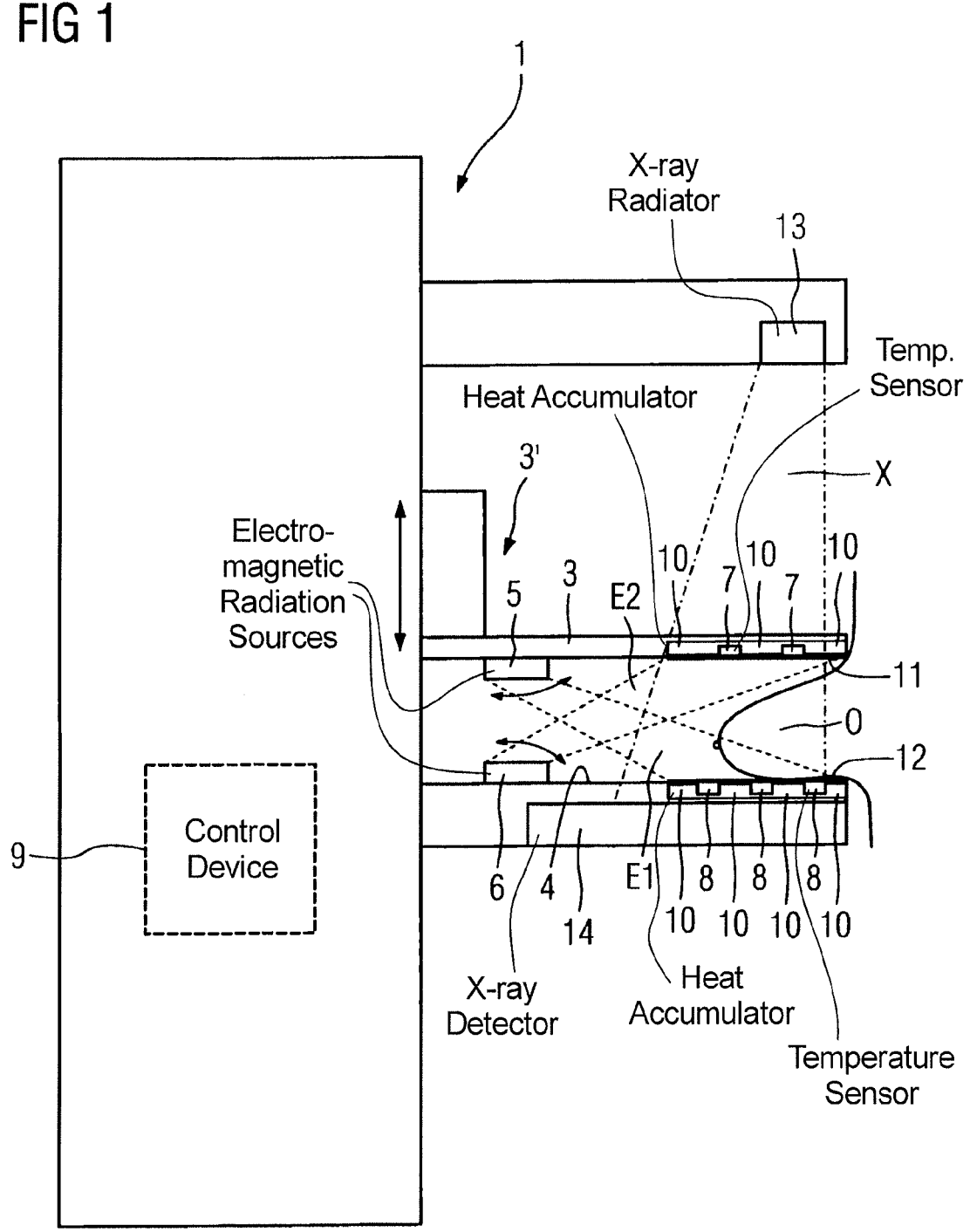
FIG. 1 is a side view of a mammography device with a first radiation source for heating of a compression plate and a second radiation source for heating of a subject table in accordance with the invention.

FIG. 1 shows a mammography device 1 with an x-ray radiator 13 and an x-ray detector 14. An x-ray region X which is permeated with x-rays upon irradiation by x-rays from the x-ray radiator 13 extends between the x-ray radiator 13 and the x-ray detector 14. Furthermore, the mammography device 1 has a compression device 3' including a compression plate 3. Together with compression plate 3, the compression device 3' is arranged such that it can be displaced relative to a stand unit (not provided with a reference character) of the mammography device 1 in order to be able to compress a breast O placed on a subject table 4 for a mammography examination.

The x-ray detector 14 of the mammography device 1 is integrated into the subject table 4, or the subject table 4 and the x-ray detector 14 form a unitary structural unit of the mammography device 1. In the exemplary embodiment, one end of the compression plate 3 (in particular the end facing away from the patient) exhibits a first radiation source 5. An electromagnetic radiation E1 which exhibits a wavelength range that reaches from an infrared spectral range up to the spectral range visible to the human eye can be radiated in a directed manner by means of the radiation source 5. In FIG. 1 the radiation direction is selected such that essentially the subject table 4 is irradiated with the electromagnetic radiation E1. The first radiation source 5 is, for example, fashioned as a red light lamp.

One end of the subject table 4 (advantageously not the end of the subject table 4 facing toward the patient) has a second radiation source 6 from which electromagnetic radiation E2 can likewise be radiated in a directed manner. The second radiation source 6 radiates the electromagnetic radiation E2 essentially in the direction of the compression plate 3 which lies essentially opposite the subject table 4.

The ray dimensioning of the electromagnetic radiation E1 or, respectively, E2 that can be radiated representing from the radiation sources 5 and 6 is adjustable. The radiation source 5 arranged on the compression plate 3 advantageously irradiates a surface region of the subject table 4 with a visible spectral portion that represents the spatial dimensions of the detector surface of the x-ray detector 14 arranged below the subject table 4. The physician thus can simply recognize in which various ways the breast O can be positioned on the subject table 4, and the detector area of the x-ray detector 14 is thereby not left uncovered.

The electromagnetic radiation E1 or E2 radiated from the first radiation source and the second radiation source heat a patient-side region of the subject table 4 or the compression plate 3. The radiation direction of the electromagnetic radiation E1 or E2 radiated by the first and the second radiation sources 5 and 6 can be adjusted manually or by means of an actuation device (not shown) controlled by a control device 9.

This is particularly advantageous when the compression plate 3 and the subject table 4 are displaced relative to one another. The radiation direction of the electromagnetic radiation E1 or E2 thus can always be adapted to the relative geometric arrangement of compression plate 3 and subject table 4. Furthermore, a radiation delimitation device (not shown) for spatial delimitation of the electromagnetic radiation E1 or E2 can be provided to adjust the radiation allowance if the electromagnetic radiation E1 or E2. The radiation delimitation device can likewise be adjusted by means of an actuation device controlled by the control device 9. For this purpose, it is advantageous to register the position and/or orientation of the compression plate 3 and/or of the subject table relative to one another or with respect to a reference so an automation of the adjustment of the radiation delimitation device is enabled.

The compression plate 3 and the subject table 4 respectively exhibit coatings 11 and 12 which absorb to a high degree the electromagnetic radiation radiated by the first and second radiation sources 5 or 6 and transduce the absorbed radiation into heat. The absorption coefficient and the thickness of the coating 11 or 12 is adapted to the wavelength spectrum of the electromagnetic radiation E1 or E2 radiated by the first radiation source 5 and from the second radiation source 6, as well as to the intensity of the radiation E1 or E2 radiated from the radiation sources 5 or 6. The coatings 11 and 12 are additionally transparent for x-rays.

The compression plate 3 and the subject table 4 each gas a heat accumulator 10 that stores the heat generated in the coating 11 or 12. A fast cooling of the coating 11 or 12 after the end of the irradiation of the coating 11 or 12 with the electromagnetic radiation E1 or E2 emanating from the first and the second radiation source 5 and 6 is thereby prevented.

Furthermore, the compression plate 3 and the subject table 4 has a number of sensors 7 or 8 in the respective warmable surface region of the compression plate 3 and the subject table 4, the sensors 7 and 8 detect the temperature of the coating 11 or 12. This is appropriate since the coated or warmable surface region is that region which at least partially comes in contact with the subject O to be examined, for example a female breast in the case of mammogram.

Excessive temperatures, for example over 40 degrees Celsius, are not desired. The sensors 7 and 8 allow monitoring of the temperature of the coating 11 and 12 so that overheating of the coating 11 or 12 is detected at an early stage. In such a case an optical or acoustic warning indication, for example, can be generated to be taken note of by the medical personnel.

The sensors 7 and 8 can also be used as a component of a control loop in order to adjust a specific temperature of the coating 11 or 12. For this purpose, the mammography device 1 has a control and regulation device 9.

For example, a temperature value for the coating 11 of the compression plate 3 and the coating 12 of the subject table 4 is stored in the control and regulation device 9, which temperature value should be reached before placement and compression of the female breast O in order to conduct the examination more comfortably for the patient. The temperature value can be selected, for example, at 37 degrees Celsius and can be supplied via an input/output device (not shown) to the control and regulation device 9.

After initiation of the heating procedure, the first and the second radiation sources 5 and 6 are activated, whereupon the first and the second radiation sources 5 or 6 radiate electromagnetic radiation E1 or E2 essentially onto the respective coated surface region of the compression plate 3 and the subject table 4. The sensors 6 and 7 detect the occurring increase of the temperature of the coating 11 or 12 due to the absorption of the x-rays. The temperature of the coating 11 or 12 is advantageously detected at regular time intervals and is supplied without contact to the control and regulation device 9.

In the control and regulation device 9 the predetermined temperature stored in the control and regulation device 9 is compared with the respective temperature detected by the sensors 7 or 8. Depending on the level of the detected temperature of the coating 11 of the compression plate 3 or the coating 12 of the subject table 4, the power of the first radiation source 5 and/or of the second radiation source 6 (which power is radiated in the form of electromagnetic radiation) is changed by the control and regulation device 9 such that the predetermined temperature of the coating 11 of the compression plate 3 and of the coating 12 of the subject table 4 is reached.

To modify the electromagnetic radiation power E1 or E2 radiated onto the coating 11 of the compression plate 3 and/or onto the coating 12 of the subject table 4, for example, the electrical power supplied to the radiation source 5 or 6 for generation of the electromagnetic radiation E1 or, respectively, E2 can be reduced or increased. For example, the radiation direction of the electromagnetic radiation E1 or E2 can also be varied so that the coating 11 or 12 is no longer exposed to the full extent, so a further heating of the coating 11 or 12 can be prevented.

The coating 11 or 12 can be of a type having properties can be altered by the application of an external electrical field and/or external magnetic field to the coating 11 or 12, such that no absorption, a reduced absorption or an increased absorption of the radiated electromagnetic radiation E1 or E2 by the coating 11 or 12 occurs, for specific field parameters of the coating 11 or 12. The control of an external field that acts on the coating 11 or 12 and influences at least one of its optical properties can likewise be effected by the control and regulation device 9.

Filters for filtering a specific wavelength range of the electromagnetic radiation radiated by the radiation source 5 or 6 also can be placed upstream of the first and/or second radiation source 5 or 6 in order to reduce the energy striking the coating 11 or 12 in the form of electromagnetic radiation E1 or E2 radiated by the respective radiation source 5 or 6. For example, given use of filters to prevent a further heating of the coating 11 or 12, the infrared wavelength range of the wavelength spectrum can in particular be significantly filtered.

Furthermore, before implementation of the mammogram the female breast can be irradiated with the first and/or second radiation source 5 or 6 in order to relax the breast tissue. The breast O thereby better adapts upon compression with the compression plate 3 between this and the subject table 4, which makes the examination more comfortable for the patient. For this purpose, in the exemplary embodiment the radiation direction of the electromagnetic radiation E1 radiated by the radiation source 5 is altered so that the radiation E1 now strikes the breast O.

This can ensue, for example, by placing the breast O on the already-heated surface region of the subject table 4 and thereby is positioned according to the projection of the detector surface, the projection being shown by means of the visible wavelength spectrum. Since the coating 12 of the subject table 4 can no longer be irradiated due to the breast O placed thereon, the radiation source 5 which is provided for heating of the subject table is used to heat the breast O. Since the heat accumulator device 10 of the subject table 4 now emits the heat to the coating 12, the coating 12 cools slowly.

Heating of the subject table 4 or of the subject O is always appropriate when the danger exists that the subject O (in particular a patient or a body part of a patient) cools. The inventive device can therefore be used on a patient who is partially unclothed in an operation or a medical procedure.

Figure 2:
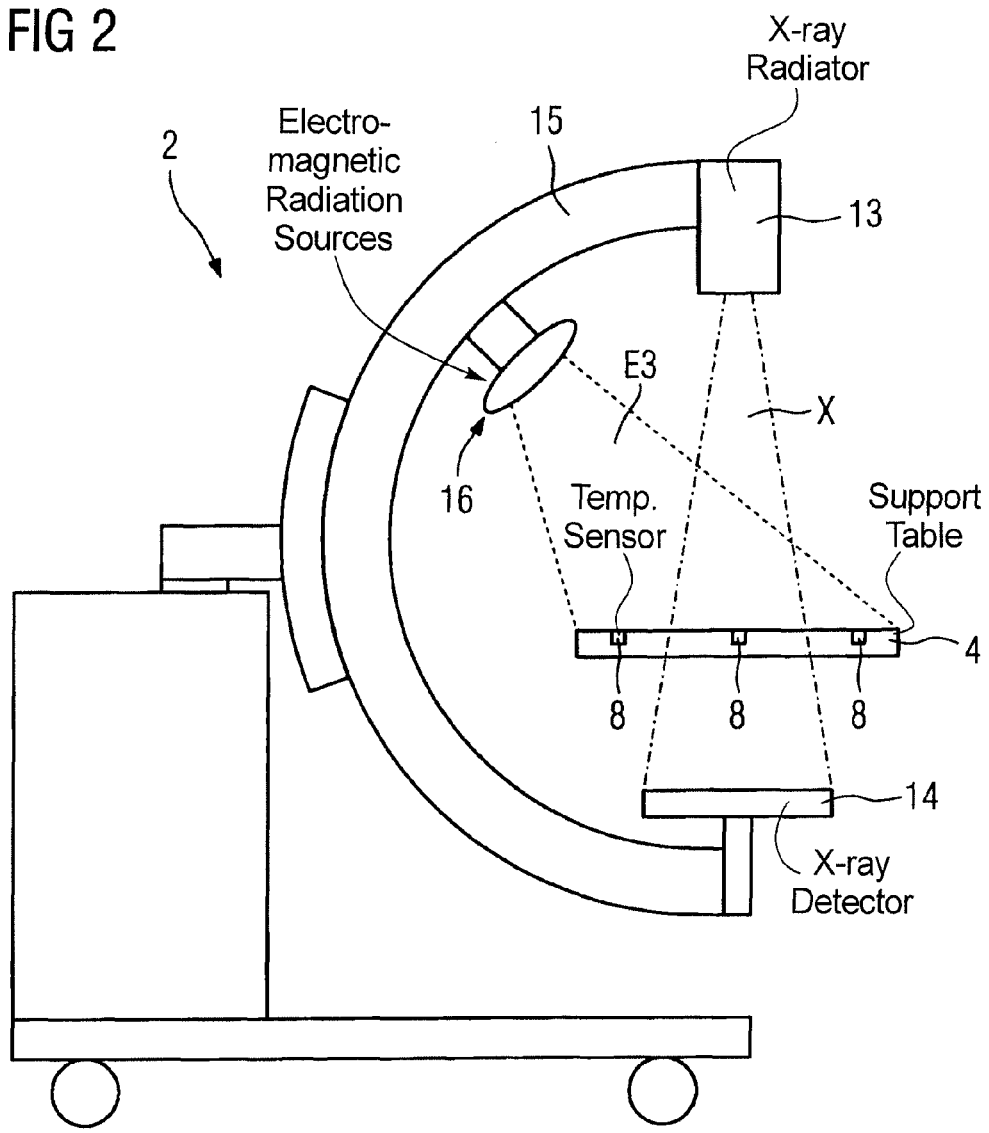
FIG. 2 is a side view of a C-arm x-ray device with a radiation source for heating of a subject table and a subject in accordance with the invention.

FIG. 2 shows an x-ray device fashioned as a movable C-arm x-ray device 2. Such a movable C-arm x-ray device 2 can, for example, be used for implementation of an x-ray examination during a medical intervention. The C-arm x-ray device 2 has an x-ray radiator 13 and an x-ray detector 14 which are supported on a C-arm 15. The x-ray region X extends between the x-ray radiator 13 and the x-ray detector 14. The x-ray region X is any spatial region which is permeated with x-rays emanating from the x-ray radiator 13 in the direction of the x-ray detector 14.

A radiation source 16 from which electromagnetic radiation E3 can be radiated in a directed manner in various directions is additionally arranged on the C-arm 15. The radiation source 16 can be displaced along the C-arm 15 and is supported such that it can rotate relative to the C-arm 15 so that the radiation direction of the electromagnetic radiation is adjustable.

In the exemplary embodiment, the C-arm x-ray device 2 is positioned next to a subject table 4, such that a patient arranged on the subject table 4 is supported between the x-ray radiator 13 arranged on the C-arm 15 and the x-ray detector 14. The radiation direction in which the radiation source 16 emits the electromagnetic radiation E3 can be adjusted manually and is aligned on a body region to be heated of the patient (not shown) or, respectively, on the subject table 4.

The body region irradiated by the electromagnetic radiation E3 can possibly also have artificial body openings, for example body openings achieved by external action by the physician. The electromagnetic radiation E3 can in particular be used to heat the irradiated body region with regard to the acceleration of blood clotting of the patient. The electromagnetic radiation E3 can also be used for curing of materials, for example of an implant implanted into the examination subject during the medical procedure that is mechanically deformable in an uncured state. In this case the subject to be heated would thus be an artificial implant introduced into the body of the patient.

The electromagnetic radiation E3 generated by the radiation source 16 can also be used for heating the subject table 4. Heating of the placement surface of the subject table 4 ensues at least in sections before the patient to be operated on or to be examined is positioned on the subject table 4, so a cooling of the patient is reduced or the examination is more comfortable for the patient.

Sensors 8 that detect the temperature of the subject table 4 at specific points in time are provided for monitoring of the temperature of the subject table 4. Data which can be transferred to a control and regulation device (not shown in FIG. 2) are associated with the detected temperatures. Monitoring of the heating of the subject table 4 or a regulation of the heating of the subject table can ensue by means of the detected temperatures.

The irradiation of the subject table 4 or of the subject by means of the electromagnetic radiation E3 emanating from the radiation source 16 can ensue in a continuous manner over a longer time span. Alternatively, the irradiation of the subject table 4 or of the subject can ensue, for example, in a pulsed manner or be manually activated and deactivated.

No coating of the subject table 4 and the material forming the subject table 4 is not particularly absorptive for heating the subject table 4 in FIG. 2. Rather, electromagnetic radiation E3 that heats a standard material used for the fashioning of a subject table 4 can be generated by means of the radiation source 16 arranged on the C-arm 15 of the C-arm x-ray device 2.

The radiation source 16 can be provided for heating the subject table 4 or a subject for a number of medical devices and subject tables. It is a cost-effective solution since no special materials and coatings are required, a radiation source 16 can simply be retrofitted for existing x-ray devices and a replacement of the radiation source 16 (for example given a defect) can be provided in a simple manner.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical device comprising:
   subject-contacting components, including a compression plate and a subject table configured to receive and compress a subject therebetween;
   at least one radiation source that emits electromagnetic radiation;
   at least one of said subject-contacting components being comprised, at least in part, of material that is elevated in temperature by interaction with said electromagnetic radiation; and
   said at least one of said subject-contacting components comprising a temperature sensor that detects the temperature of said at least one of said subject-contacting components.

2. A medical device as claimed in claim 1 wherein said radiation source emits said electromagnetic radiation with a wavelength spectrum comprising a first sub-range in the infrared spectral range and a second sub-range in the humanly visible spectral range.

3. A medical device as claimed in claim 2 wherein said electromagnetic radiation source embodies humanly perceptible information in said electromagnetic radiation in said second sub-range, projected onto said at least one of said subject-contacting components.

4. A medical device as claimed in claim 1 comprising a control device connected to said temperature sensor that controls a temperature increase of said at least one of said subject-contacting components dependent on the temperature detected by said temperature sensor.

5. A medical device as claimed in claim 1 comprising a regulator device connected to said temperature sensor that regulates a temperature increase of said at least one of said subject-contacting components dependent on the temperature detected by said temperature sensor.

6. A medical device as claimed in claim 1 wherein said at least one of said subject-contacting components comprises a structure that slows decay of said elevation in temperature that occurs after said interaction with said electromagnetic radiation ceases.

7. A medical device as claimed in claim 1 wherein said radiation source is adjustable to allow adjustment of a direction in which said electromagnetic radiation is emitted from said radiation source.

8. A medical device as claimed in claim 7 wherein said radiation source allows adjustment of said direction perpendicular to a surface normal of said at least one of said subject-contacting components.

9. A medical device as claimed in claim 1 wherein said at least one of said subject-contacting components comprises a plate having a coating covering at least a portion of said plate in a region struck by said electromagnetic radiation, said coating promoting conversion of said electromagnetic radiation into heat to produce said elevation in temperature of said at least one of said subject-contacting components.

10. A medical device as claimed in claim 9 wherein said electromagnetic radiation exhibits a wavelength spectrum, and wherein said coating exhibits optical properties adapted to said wavelength spectrum of said electromagnetic radiation.

11. A medical device as claimed in claim 9 wherein said coating is substantially transparent to said x-rays.

12. A medical device as claimed in claim 1 wherein said at least one of said subject-contacting components comprises a plate comprised of a material that promotes conversion of said electromagnetic radiation into heat to produce said increase in temperature of said at least one said subject-contacting components.

13. A medical device as claimed in claim 12 wherein said electromagnetic radiation has a wavelength spectrum, and wherein said material comprising said plate exhibits optical properties adapted to said wavelength spectrum.

14. A medical device as claimed in claim 13 wherein said material comprising said plate is substantially transparent to x-rays.

15. A medical device as claimed in claim 1 wherein said at least one of said subject-contacting components is configured to transfer said elevation in temperature to the subject in contact with said at least one of said subject-contacting components.

16. A medical device as claimed in claim 15 wherein said subject exhibits optical properties, and wherein said radiation source emits said electromagnetic radiation with a radiation characteristic, selected from the group consisting of intensity and wavelength spectrum that is adapted to said optical properties of the subject.

17. A medical device as claimed in claim 1 wherein said compression plate and said support table are configured to receive and compress a female breast therebetween.

18. A medical device as claimed in claim 17 comprising an x ray imaging system that produces an x-ray image of the female breast compressed between said compression plate and said support plate.

* * * * *